United States Patent [19]

Johnston et al.

[11] Patent Number: 4,523,017

[45] Date of Patent: Jun. 11, 1985

[54] PREPARATION OF TRIFLUOROMETHYL PYRIDINYLOXYPHENOXY PROPANOIC ACIDS AND PROPANOLS AND DERIVATIVES THEREOF

[75] Inventors: Howard Johnston, Walnut Creek; Lillian H. Troxell, Antioch, both of Calif.

[73] Assignee: The Dow Chemical Company, Midland, Mich.

[21] Appl. No.: 529,178

[22] Filed: Sep. 2, 1983

Related U.S. Application Data

[63] Continuation of Ser. No. 357,346, Mar. 11, 1982, abandoned, which is a continuation of Ser. No. 918,550, Jun. 23, 1978, abandoned, which is a continuation-in-part of Ser. No. 817,943, Jul. 22, 1977, abandoned.

[51] Int. Cl.$^3$ .................................... C07D 213/64
[52] U.S. Cl. .................................... 546/302; 546/291; 546/300
[58] Field of Search .................. 546/302, 291, 300

[56] References Cited

U.S. PATENT DOCUMENTS

| | | | |
|---|---|---|---|
| 3,244,722 | 4/1966 | Johnston et al. | 546/303 |
| 3,711,486 | 1/1973 | Torba | 71/94 X |
| 4,046,553 | 9/1977 | Takahashi et al. | 71/94 |

OTHER PUBLICATIONS

Kobayashi, Y., et al., *Chem. Pharm. Bull.* (Japan), 19(3), 624–627, (1971).

Dainter, R., et al., *Tett. Lett.* 25, (#49), 5693–5696, (1984).

*Primary Examiner*—Richard A. Schwartz

[57] ABSTRACT

2-((4-Pyridinyl-2-oxy)phenoxy)propanoic acids, amides, salts and esters thereof, and nitriles derived therefrom and 2-((4-pyridinyl-2-oxy)phenoxy) propanols and esters and ethers thereof, and the corresponding 2-((4-pyridinyl-2-thio)phenoxy) propanoate and propanol compounds, all having trifluoromethyl substitution in at least one of the 3- and the 5-position in the pyridine ring with or without additional substitution at the converse position in the pyridine ring according to the following formula, are useful as herbicidal agents:

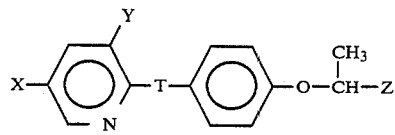

wherein the various substituents are defined hereinbelow.

9 Claims, No Drawings

PREPARATION OF TRIFLUOROMETHYL PYRIDINYLOXYPHENOXY PROPANOIC ACIDS AND PROPANOLS AND DERIVATIVES THEREOF

CROSS-REFERENCE TO RELATED APPLICATION

This application is a continuation of application Ser. No. 357,346, filed Mar. 11, 1982, now abandoned, which in turn is a continuation of application Ser. No. 918,550, filed June 23, 1978 which in turn is a continuation-in-part of application Ser. No. 817,943, filed July 22, 1977 now abandoned.

BACKGROUND OF THE INVENTION

1. Field of the Invention

The invention relates (a) to novel pyridinyloxyphenoxy propanoic acids, salts and esters thereof and pyridinyloxyphenoxy propanols and esters and ethers thereof, and propionitriles, and the corresponding 2-((4-pyridinyl-2-thio)phenoxy)propanoate and propanol compounds, (b) to herbicidal compositions of such novel compounds and (c) to preemergent and postemergent methods of using such compounds for the control of grassy weeds in non-crop areas as well as in the presence of some specified valuable crops.

2. Description of the Prior Art

Belgian Pat. No. 834,495, issued Feb. 2, 1976, as well as the published German patent application equivalent thereto, viz., No. 2,546,251, published Mar. 29, 1976, describe 2-((4-pyridinyl-2-oxy)phenoxy)alkanoic acids, salts and esters having halo substitution in the 3 and/or 5 ring positions in the pyridine ring. Published Japanese patent application No. 129313/75, filed in Japan Oct. 29, 1975 teaches pyridyloxyphenoxypropanols and esters thereof, while published Japanese patent application No. 064,160/75, filed May 30, 1975, teaches pyridyloxyphenoxypropionitrile compounds. The patent disclosures do not teach or suggest, however, trifluoromethyl substitution at any position in the pyridine ring of such compounds. These prior art compounds are disclosed to be active herbicides useful in the control of grassy weeds.

SUMMARY OF THE INVENTION

The present invention is directed to novel pyridinyloxyphenoxy propanoic acids, salts and esters having trifluoromethyl substitution in the pyridine ring according to the following formula:

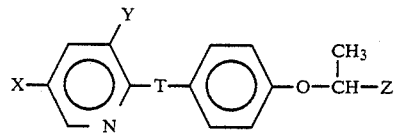

wherein:
T is oxygen or sulfur;
X is Cl, Br or $CF_3$;
Y is H, Cl, Br or $CF_3$, provided at least one of X and Y is $CF_3$;
Z is

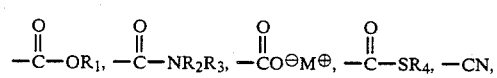

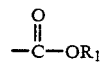

$R_1$ is H, $C_1$-$C_8$ alkyl, benzyl, chlorobenzyl or $C_3$-$C_6$ alkoxyalkyl;
$R_4$ is $C_1$-$C_4$ alkyl;
$R_5$ is H or $C_1$-$C_4$ alkyl;
$R_6$ is $C_1$-$C_7$ alkyl;
M is —$NHR_2R_3R_7$, Na, K, Mg or Ca;
$R_2$ and $R_3$ are each independently selected from $R_7$ or —$OCH_3$, provided both $R_2$ and $R_3$ cannot be simultaneously —$OCH_3$ and neither is —$OCH_3$ in —$NHR_2R_3R_7$; and
$R_7$ is H, $C_1$-$C_4$ alkyl or $C_2$-$C_3$ hydroxyalkyl.

The compounds of the above formula, hereinafter referred to for convenience as "active ingredients", have been found to be especially active as herbicides for the control of undesired vegetation, for example, grassy or graminaceous weeds. Accordingly, the present invention also encompasses compositions containing one or more active ingredients as well as preemergent and postemergent methods of controlling undesired plant growth, especially in the presence of valuable crops. Such methods comprise applying a herbicidally-effective amount of one or more active ingredients to the locus of the undesired plants, that is, the seeds, foliage, rhizomes, stems and roots or other parts of the growing plants or soil in which the plants are growing or may be found.

DETAILED DESCRIPTION OF THE INVENTION

The term "herbicide" is used herein to mean an active ingredient which controls or adversely modifies the growth of plants because of phytotoxic or other effects substantial enough to seriously retard the growth of the plant or further to damage the plant sufficiently to kill the plant.

By "growth controlling" or "herbicidially-effective" amount is meant an amount of active ingredient which causes a modifying effect and includes deviations from natural development, killing, regulation, desiccation, retardation, and the like.

The term "plants" is meant to include germinant seeds, emerging seedlings, rhizomes and established vegetation.

The terms "$C_1$-$C_4$ alkyl" or "$C_1$-$C_7$ alkyl", e.g., refer to different size alkyl groups which may be straight or branched.

The term "$C_3$-$C_6$ alkoxyalkyl", for example, is meant to refer to an alkoxyalkyl group having three to six carbon atoms, the alkyl portion being straight or branched.

The active ingredients of the present invention are generally oils or crystalline solids at ambient temperatures which are soluble in many organic solvents commonly employed as herbicidal carriers. The active ingredients of the above formula wherein T is oxygen, X is $CF_3$, Y is Cl or H, and Z is $$-\overset{O}{\underset{\|}{C}}-OR_1$$

wherein $R_1$ is $C_1$-$C_8$ alkyl constitute preferred embodiments of the present invention. The active ingredients of the above formula wherein T is oxygen, X is CF₃, Y is Cl, Br, CF₃ or hydrogen, Z is

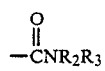

wherein $R_2$ and $R_3$ are each independently hydrogen—OCH₃, or $C_1$–$C_4$ alkyl constitute additional preferred embodiments. Yet additional preferred embodiments are the present compounds wherein T is sulfur, X is CF₃, Y is Cl, and Z is

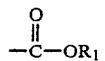

wherein $R_1$ is H or $C_1$–$C_8$ alkyl.

The active ingredients, i.e., new compounds, of the present invention wherein T is oxygen are readily prepared by the reaction of 4-hydroxyphenoxy-2-propanoic acid or an ester thereof with a substituted pyridine having the requisite substitution in the 3- and-/or 5-ring positions in addition to 2-halo substitution. The pyridine compound used as starting material is itself prepared from a 2-halopyridine compound, generally the 2-chloro substituted compound, having trichloromethyl substitution in either or both of the 3- and 5-ring positions in addition to any desired chloro or bromo substitution at the 3- or 5-positions, if not occupied by a CCl₃ group, by reacting the pyridine compound with a fluorinating material such as antimony trifluoride whereupon the trichloromethyl group or groups are converted to trifluoromethyl groups, as well understood in the art.

The new compounds of the present invention wherein T is sulfur are similarly prepared by the reaction of 4-mercaptophenoxy-2-propanoic acid or an ester thereof with an appropriate substituted pyridine in substantially the same manner as described above.

The reaction between such a substituted pyridine and the said hydroxy- or mercapto-phenoxy propanoic acid is rather readily carried out in a polar solvent such as dimethyl sulfoxide to which has been added a small amount of aqueous or powdered sodium hydroxide. Reaction is usually carried out at a temperature in the range of about 70° to about 125° C. over a period of about 1 to 3 hours under ambient atmospheric pressure. The reaction mixture is then allowed to cool and is poured into a quantity of cold water and acidified with hydrochloric acid, whereupon the product precipitates and is separated and purified as may be required.

The propanoate esters of the present invention may be prepared in substantially the same manner as set forth above for the propanoic acids, using the requisite ester of 4-hydroxyphenoxy-2-propanoic acid or 4-mercaptophenoxy-2-propanoic acid to react with the appropriately substituted 2-halopyridine. Or, if desired, the appropriate propanoic acid of the invention is esterified by first converting to the acid chloride with thionyl chloride and then reacting the acid chloride with the appropriate alcohol, or, mercaptan, such as, ethyl mercaptan, propyl mercaptan or butyl mercaptan, according to generally accepted procedures or the classic method of reacting an alcohol and an acid in the presence of a little sulfuric acid may be followed.

The propanoic acid compounds of the invention after conversion to the acid chloride may also be reacted with (a) ammonia to form the simple amide, (b) with an alkyl amine to form an N-alkyl amide or N,N-dialkyl amide, or (c) with a methoxy amine to form an alkoxy amide.

The simple amide serves as preferred starting material for the manufacture of the present nitriles, which are obtained upon reaction of the amide is phosphorous oxychloride.

The propanoate metal salts of the invention are prepared from the propanoic acid form of the compound by simply reacting the carboxylic acid with the requisite inorganic base, such as NaOH, KOH, Ca(OH)₂ or Mg(OH)₂. The amine salts are prepared by reacting the propanoic acid compound with the requisite amine, for example, triethanolamine or trimethylamine.

The compounds according to the invention which are substituted propanols are prepared preferably from one of the above described esters of the propanoic acid form of the compound, such as the methyl ester, by reaction of the ester with sodium borohydride in a polar solvent medium such as methanol, reaction being carried out initially at a temperature below about 30° C. during an initial period of 1 to 2 hours after which the temperature is brought to about 50° to 60° C. and the solvent then stripped off. The reaction product is then admixed with water and extracted with a water-immiscible organic solvent. Removal of the solvent leaves an oily product.

Esterification of such alcohol is carried out according to methods generally known in the art in which, e.g., an acid chloride is reacted with the alcohol in solvent medium in the presence of a hydrogen chloride acceptor, such as triethylamine. The hydrochloride salt is filtered off and the solvent stripped, leaving an oily product.

Ethers of the alcohols of the invention are prepared by reacting the alcohol with, e.g., sodium hydride in a polar solvent such as dimethyl formamide at a temperature of about 35° to 60° C., after which an alkyl bromide is added to the reaction mixture and heated to 75° to 100° C. for one to two hours. The solvent medium is then stripped off under reduced pressure and the crude product is poured into cold water and final product taken up with water immiscible solvent such as heptane. The solvent, on being stripped off, leaves an oily product.

In an alternate process for making the present propanoic acid compounds, a salt, e.g., the sodium salt, of 4-methoxyphenol, or of 4 mercaptophenol, is dissolved in a solvent such as dimethyl sulfoxide and the requisite trifluoromethyl-substituted 2-chloropyridine is added to the solution of the methoxy phenol and reacted in the presence of a little aqueous sodium hydroxide at a temperature in the range of about 70° to 130° C. and over a time interval of about 30 to 45 minutes. The reaction mixture is then cooled somewhat and poured over ice. The solid product is filtered off and washed with water and taken up in a solvent mixture and reprecipitated therefrom. The methoxy group, if present, is then cleaved off the phenyl ring by refluxing the compound in 48% by weight HBr for about an hour and after purification, precipitated from acidic solution and recovered, as by filtration, and dried. The trifluoromethyl-substituted 2-pyridinyloxy phenol, or trifluoromethyl-substituted 2-pyridinylthiophenol, is then dissolved in a solvent such as dimethyl sulfoxide, anhydrous powdered sodium hydroxide is added thereto and reacted therewith for a few minutes at about 75° to 85° C. Then an ester, such as the ethyl ester, of 2-bromopropanoic acid is added to the reaction mixture and stirred for a time, such as about half an hour, at approximately 100° C. or up to about 2 hours in the case of the sulfur bridged compound. The reaction mixture is then allowed to cool and poured over ice or simply into cold water whereupon an oily layer separates which can be recovered by taking up in a water-immiscible solvent and subsequently stripping the solvent off leaving an oily product. The product so obtained will be the alkyl ester of the propanoic acid compound. In carrying out the several reactions of this alternate process, the reactants are usually mixed with a carrier medium, such as, for example, methylethyl ketone, methylisobutyl ketone or an aprotic polar solvent such as dimethylformamide, dimethylacetamide, dimethylsulfoxide, N-methylpyrrolidone, hexamethylphosphoramide or sulfolane. The first step condensation is generally carried out at a temperature of at least 50° C., preferably about 70° to about 150° C. and during a reaction period of about 1 to about 20 hours, preferably about 1 to about 10 hours. The second condensation reaction is carried out under similar reaction conditions except that the reaction is usually accomplished in a shorter period of time such as about 0.5 to 10 hours, typically using one of the aprotic solvents such as dimethylsulfoxide as reaction medium. The dealkylation step, where employed, is carried out using as a suitable dealkylation agent, a hydro acid such as hydrobromic acid or hydriodic acid employed as a concentrated aqueous solution of about 40 to about 60 percent by weight concentration. Reaction is carried out at a reflux temperature which usually falls in the range of about 75° to about 150° C. but preferably is about 100° C. to 140° C. The dealkylation reaction is generally completed in about 1 to about 10 hours.

The active ingredients of the above formula wherein Z is —CH$_2$OOCR$_6$ are readily prepared from the requisite 2-propanoic acid compound, prepared as described above, followed by esterification with a primary alcohol conveniently available, such as methanol, and in the presence of a small amount of sulfuric acid, after which the ester is reduced to the alcohol upon reaction with sodium borohydride in aqueous medium and at close to ambient room temperature. After removal of excess primary alcohol the product is extracted from the reaction mixture with a water-immiscible solvent or solvent mixture such as methylene chloride-heptane. Finally, the solvent is stripped off and removed under reduced pressure leaving the product which is usually an oil.

The so-produced substituted propanol is esterified, if desired, by reacting it with the acid chloride of the esterifying acid in solvent medium, such as toluene, containing in admixture, an HCl acceptor such as triethyl amine. Reaction proceeds steadily over about a 1 to 1.5 hour period at a temperature in the range of about 100° to about 135° C. The precipitated trialkylamine hydrochloride is filtered off and the solvent medium stripped off. Subsequently, the residue is preferably washed with water and then taken up in hot heptane, dried, and the heptane distilled off leaving an oily product.

The substituted propionitriles of the invention are prepared using the propanoic acid compound as the starting material. The carboxylic acid is reacted with thionyl chloride to form the acid chloride which is in turn reacted with NH$_4$OH to produce the amide. The amide is reacted with POCl$_3$ to form the nitrile.

The following examples illustrate the present invention and the manner by which it can be practiced but as such are not to be construed as limitations upon the overall scope of the invention.

EXAMPLE 1

2-Chloro-5-(trichloromethyl)pyridine (23.0 grams ("g"); 0.1 mole) was mixed with antimony trifluoride (22.3 g; 0.125 mole) and then chlorine gas (9.0 g; 0.126 mole) was passed into the stirred mixture over a period of 8 minutes during which time the temperature rose from ambient to 100° C. The reaction mixture was stirred for an additional 20 minutes before adding 25 milliliters of concentrated HCl plus 27 milliliters of water and steam distilling off any unreacted starting material and volatile chlorides and fluorides. Thereafter, pentane was added to the receiver vessel to take up the solid product which was subsequently recovered by distilling off the solvent.

The crystalline product obtained had a melting temperature of 30°–1° C. and upon analysis was found to contain 39.56% carbon; 1.78% hydrogen; 7.72% nitrogen; and 19.42% chlorine. The theoretical composition for 2-chloro-5-(trifluoromethyl)pyridine is 39.69% carbon; 1.66% hydrogen; 7.72% nitrogen; and 19.53% chlorine.

The following substituted pyridines are prepared in a similar manner:

| Ring Substituents on Pyridine | | | |
|---|---|---|---|
| 2 | 3 | 5 | Physical Property |
| Cl | CF$_3$ | CF$_3$ | (B.P.) 94–96° C. @ 109 mm Hg |
| Cl | Cl | CF$_3$ | (B.P.) 50–51° C. @ 21 mm Hg |
| Cl | CF$_3$ | Cl | $n^{25°}$ = 1.4825 |
| Cl | Br | CF$_3$ | |

EXAMPLE 2

2-(4-hydroxyphenoxy)propanoic acid (2.35 g; 0.0129 mole) was dissolved in dimethylsulfoxide (16 ml) and then a solution of sodium hydroxide (1.06 g; 0.026 mole) in 3.5 ml of water was added. This mixture was stirred and heated to about 60° C. over a 20 minute period in order to insure formation of the disodium salt. Next a solution of 2-chloro-3,5-bis(trifluoromethyl)pyridine (2.73 g; 0.0129 mole) in 8 ml of dimethylsulfoxide reaction medium was added over a 3 minute period and the mixture then warmed to 110° C. in 35 minutes. The mixture was then heated at 105°–110° C. for an additional 45 minutes, allowed to cool for 30 minutes, and then poured into cold water. The resulting crude, gummy product was taken up in hot toluene, treated with activated charcoal, and filtered. The toluene was then flashed off and the product was extracted with pentane which was chilled resulting in the separation of a crystalline product having a melting temperature of 80.5°–83° C. The product was found on analysis to contain 48.87% carbon; 3.14% hydrogen; and 3.59% nitrogen. The theoretical composition for 2-(4-(3,5-bis(-trifluoromethyl)-2-pyridinyl)oxy)phenoxy)propanoic acid is 48.62% carbon; 2.80% hydrogen; and 3.54% nitrogen, thus confirming the obtention of the anticipated product.

In a manner similar to the foregoing procedure, using the requisite starting materials, the following 4-pyridinyloxyphenoxy propanoic acid compounds of the invention are prepared:

| Ring Substituents On Pyridine | | Melting Temperature, °C. | Elemental Analysis, % By Weight* | | | |
|---|---|---|---|---|---|---|
| 3 | 5 | | C | H | N | Cl |
| Cl | $CF_3$ | 105.5–107 | 49.73 (49.81) | 3.25 (3.06) | 3.78 (3.87) | 9.66 (9.80) |
| $CF_3$ | $CF_3$ | 80.5–83 | 48.87 (48.62) | 3.14 (2.80) | 3.59 (3.54) | — |
| — | $CF_3$ | 97–100 | 54.91 (55.05) | 3.77 (3.70) | 4.27 (4.28) | — |
| $CF_3$ | Cl | 115–118 | 49.79 (49.81) | 3.21 (3.06) | 3.99 (3.87) | 9.77 (9.80) |
| Br | $CF_3$ | | | | | |
| $CF_3$ | Br | | | | | |

*Theoretical composition shown in parenthesis

EXAMPLE 3

3,5-bis(trifluoromethyl)-2-pyridinyloxy-4-phenoxypropanoic acid (16.0 g; 0.0405 mol) was refluxed with 110 ml of thionyl chloride for 26 minutes and then the unreacted thionyl chloride was distilled off. The resulting acid chloride was put into 40 ml of methanol. Triethylamine (5.2 g; 0.0514 mol) was put into 75 ml of methanol. The acid chloride solution was then added and the reaction mixture was taken to reflux and refluxed for 30 minutes. The methanol was removed by distillation and the crude product was washed with water and taken up in heptane. The heptane was removed and 15 grams of amber oil was obtained which had a refractive index of 1.4832 at 25° C.

The product had the following elemental analysis:

| | C | H | N |
|---|---|---|---|
| Calculated | 49.88 | 3.20 | 3.42 |
| Found | 49.97 | 3.20 | 3.52 |

These results confirm the obtention of methyl 2-(4-((3,5-bis(trifluoromethyl)-2-pyridinyl)oxy)phenoxy)-propanoate.

Other active ingredients of the present invention are similarly prepared by employing procedures analogous to those set forth in the above example and the foregoing teachings of the specification. Such other active ingredients include the following compounds:

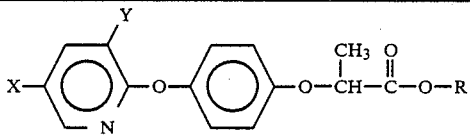

| X | Y | R | Refractive Index @ 25° C. | Elemental Analysis, % By Weight* | | | |
|---|---|---|---|---|---|---|---|
| | | | | C | H | N | Cl |
| $CF_3$ | $CF_3$ | —$(CH_2)_7CH_3$ | 1.4743 | 55.65 (56.80) | 5.02 (5.36) | 2.96 (2.76) | — |
| Cl | $CF_3$ | —$(CH_2)_3CH_3$ | 1.5076 | 54.49 (54.62) | 4.69 (4.58) | 3.41 (3.35) | 8.60 (8.49) |
| $CF_3$ | Cl | —$(CH_2)_3CH_3$ | 1.5080 | 54.61 (54.62) | 4.65 (4.58) | 3.34 (3.35) | 8.47 (8.49) |
| Br | $CF_3$ | —$C_2H_5$ | | | | | |
| $CF_3$ | H | —$CH_2$—⟨⟩—Cl | 1.5432 | 49.94 (51.07) | 2.76 (2.68) | 7.25 (7.44) | |
| $CF_3$ | Br | —$CH_2$—⟨⟩—$CH_3$ | | | | | |
| $CF_3$ | H | —$(CH_2)_2CH_3$ | | | | | |
| $CF_3$ | Cl | —$CH_2$—$CH_2$—$OC_4H_9$ | | | | | |
| $CF_3$ | — | $\pm(CH-CH_2-O)_{10}\pm(CH_2-CH_2O)_{15}$—H, $\vert$ $CH_3$ | | | | | |
| $CF_3$ | $CF_3$ | —$(CH_2CH_2O)_{15}$H | | | | | |
| $CF_3$ | Cl | —$(CH-CH_2O)_{15}$—H, $\vert$ $CH_3$ | | | | | |
| $CF_3$ | Cl | —$CH_2$—$CH_2$—O—$CH_3$ | | | | | |
| $CF_3$ | Cl | —$(CH_2)_2$—O—$(CH_2)_3CH_3$ | 1.5061 | 54.61 | 5.02 | 3.03 | 7.68 |

*Theoretical composition shown in parenthesis

EXAMPLE 4

To 5.0 g (0.0138 mole) of 2-(4-(3-chloro-5-(trifluoromethyl)pyridinyl-2-oxy)phenoxy)propanoic acid was added 30 ml of $SOCl_2$ and the mixture heated at reflux for about 20 minutes after which unreacted $SOCl_2$ was removed on a still under water aspirator vacuum. The resulting syrup was added to a stirred solution of 30 ml (0.028 mole) of concentrated aqueous $NH_4OH$ in 40 ml of acetonitrile. The mixture was stirred at a temperature of 25° C. for 15 minutes and filtered, thus recovering crystals of solid product which had formed. The recovered crystals exhibited a melting temperature of 140°–42° C. On elemental analysis, the crystals were found to contain 49.50% carbon; 3.44% hydrogen; 10.01% chlorine; and 7.76% nitrogen. Theoretical composition for 2-(4-(3-chloro-5-(trifluoromethyl)pyridinyl-2-oxy)phenoxy)propionamide is 49.94% carbon; 3.35% hydrogen; 9.83% chlorine; and 7.76% nitrogen.

Other 2-((4-(trifluoromethyl substituted)-2-pyridinyl)oxy)phenoxypropionamides of the invention are prepared using procedures similar to the foregoing using the requisite starting materials. Such active ingredients include the following compounds:

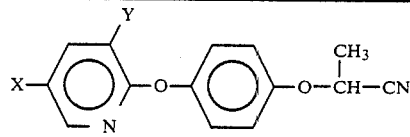

| X | Y | Melting Temperature °C. | Elemental Analysis, % By Weight* | | | |
|---|---|---|---|---|---|---|
| | | | C | H | N | Cl |
| CF$_3$ | Cl | 49–52 | 52.71 (52.27) | 3.07 (2.94) | 10.47 (10.35) | 7.47 (8.17) |
| CF$_3$ | — | 38–40 | 58.16 (58.44) | 3.79 (3.57) | 8.81 (9.08) | — |

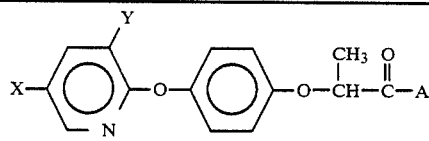

| X | Y | A | Melting Temperature °C. | Elemental Analysis, % By Weight* | | | |
|---|---|---|---|---|---|---|---|
| | | | | C | H | N | Cl |
| Cl | CF$_3$ | —NH$_2$ | 151–152 | 48.56 (49.94) | 3.37 (3.35) | 7.57 (7.77) | 9.57 (9.83) |
| CF$_3$ | Cl | —NHCH$_3$ | 146–147 | 51.14 (51.78) | 3.73 (3.76) | 7.37 (7.47) | 9.63 (9.46) |
| CF$_3$ | CF$_3$ | —N(n-C$_4$H$_9$)$_2$ | (n$^{25°}$ = 1.4844) | 56.30 (56.91) | 5.48 (5.57) | 5.06 (5.33) | — |
| CF$_3$ | — | —N(CH$_3$)$_2$ | (n$^{25°}$ = 1.5247) | 57.99 (57.6) | 5.04 (4.84) | 7.74 (7.9) | — |
| CF$_3$ | — | —NH$_2$ | 69–70 | 55.3 (55.22) | 4.09 (4.02) | 8.62 (8.58) | |
| CF$_3$ | CF$_3$ | —NH$_2$ | 150.5–152 | 48.78 (48.75) | 3.17 (3.05) | 6.96 (7.1) | |
| CF$_3$ | Br | —NH$_2$ | — | | | | |
| CF$_3$ | Cl | —NHCH$_3$ | 146–147 | 51.19 (51.28) | 3.73 (3.76) | 7.37 (7.47) | 9.63 (9.46) |
| CF$_3$ | — | —NHCH$_3$ | | | | | |
| CF$_3$ | Cl | —NH—nC$_4$H$_9$ | | | | | |
| Br | CF$_3$ | —NH—nC$_3$H$_7$ | | | | | |
| CF$_3$ | — | —NH—OCH$_3$ | | | | | |
| CF$_3$ | Cl | —NHCH$_2$CH$_2$OH | (n$^{25}$ = 1.5434) | 50.71 (50.44) | 3.81 (3.98) | 6.41 (6.92) | 8.96 (8.76) |
| CF$_3$ | Cl | —NH—OCH$_3$ | 135–6 | | | | |

*Theoretical composition shown in parenthesis

EXAMPLE 5

5-chloro-3-trifluoromethyl-2-pyridinyloxy-4-phenoxypropionamide (4.5 g; 0.01248 mols) was refluxed with 20 ml of phosphorous oxychloride for a total time of 1 hour and 45 minutes. The POCl$_3$ was distilled off and the remaining reaction mixture was poured over ice and extracted with heptane. On cooling a crystalline product was obtained with a melting range of 61.5–62.5° C. The anticipated product was 2-(4-(5-chloro-3-(trifluoromethyl)-2-pyridinyl)oxy)phenoxy)propionitrile. The following elemental analysis was obtained:

| | C | H | N | Cl |
|---|---|---|---|---|
| Calculated | 52.57% | 2.94% | 8.18% | 10.35% |
| Found | 52.48% | 3.01% | 8.17% | 10.14% |

Other active nitrile compounds of the present invention are similarly prepared by employing the procedures analogous to those set forth in the above example and the foregoing teaching of the specification. Such other active ingredients include the following compounds:

| X | Y | Melting Temperature °C. | C | H | N | Cl |
|---|---|---|---|---|---|---|
| CF$_3$ | CF$_3$ | 54–55 | 49.94 (51.07) | 2.76 (2.68) | 7.25 (7.44) | |
| Br | CF$_3$ | — | | | | |
| Cl | CF$_3$ | 61.5–62.5 | 52.48 (52.57) | 3.01 (2.94) | 8.17 (8.18) | 10.14 (10.35) |

*Theoretical composition shown in parenthesis

EXAMPLE 6

In each of a series of metal salt preparations 60 milligrams (mg) of one of the propanoic acids of the invention was stirred into several milliliters (ml) of water and (an aqueous solution of base added thereto in the amount needed for neutralization plus a slight excess estimated to be 10% excess upon obtaining a color change to yellow green in universal indicator. The propanoic acids, the molar amounts employed, the bases employed and the estimated amounts of such bases are tabulated as follows, the propanoic acid being identified by ring substitution on the pyridinyl ring:

| Ring Substituents | | Propanoic | | mg of |
|---|---|---|---|---|
| 5 | 3 | Acid, mols. | Base | Base (estimated) |
| CF$_3$ | — | 0.183 | NaOH | 7.34 |
| CF$_3$ | Cl | 0.165 | KOH | 9.25 |
| CF$_3$ | CF$_3$ | 0.152 | *NH$_4$OH | 5.32 |

*The NH$_4$OH was employed in the form of concentrated ammonium hydroxide.

The aqueous solutions so obtained are conveniently used in herbicidal applications with or without further dilution. The salts may be recovered by evaporation of the water from the solutions and purified by careful recrystallization, if desired.

The magnesium and calcium salts of the identified propanoic acids as well as the other propanoic acids of the invention are prepared in substantially the manner described

EXAMPLE 7

In each of a series of amine salt preparations 60 mg of one of the propanoic acids of the invention was stirred into several ml of water and a solution of alkyl amine or alkanolamine added thereto in the amount needed for neutralization plus an estimated 10 percent excess of base believed to be reached upon titrating to the yellow-green color of universal indicator. The propanoic acids, here identified by ring substituents, the molar amount of propanoic acid, the base employed and the estimated amounts of each base, are tabulated as follows:

| Ring Substituents | | Propanoic | | mg of |
|---|---|---|---|---|
| 5 | 3 | Acid, mols. | Base | Base (estimated) |
| CF$_3$ | — | 0.183 | NH$_2$C$_2$H$_5$OH | 11.19 |
| CF$_3$ | Cl | 0.165 | (C$_2$H$_5$)$_3$N | 16.68 |
| Cl | CF$_3$ | 0.165 | C$_2$H$_5$NH$_2$ | 7.43 |

The aqueous solutions so obtained are conveniently used in herbicidal applications with or without further dilution. The salts may be recovered by evaporation of water from the solutions and purified by careful recrystallization, if desired.

The preparation of other amine salts such as the triethanolamine and diethanolamine salts, the tripropylamine salt and the butylamine salts are prepared in substantially the manner described above.

EXAMPLE 8

Sodium borohydride (6.35 g; 0.1716 mols) was dissolved in 25 ml of water and added over a ten minute period to a solution of methyl 2-(4-((3,5-bis(trifluoromethyl)-2-pyridinyl)oxy)phenoxy)propionate (11.7 g; 0.02859 mols) dissolved in 155 ml of warm methanol. During the addition the temperature was kept between 25° and 30° C. The mixture was allowed to stir at room temperature for 40 minutes and was then allowed to warm to 42° C. over a 25 minute period. The methanol was then removed by distillation and cold water was added to the crude product which was then extracted with a methylene chloride-heptane mixture. The solvents were distilled off leaving an orange colored oil with an index of refraction of 1.5028 at 25° C. The anticipated product was 2-(4-((3,5-bis(trifluoromethyl)-2-pyridinyl)oxy)phenoxy)-propanol. The product had the following elemental analysis:

| | C | H | N |
|---|---|---|---|
| Calculated | 50.40% | 3.44% | 3.67% |
| Found | 51.01 | 3.64 | 3.86 |

Other pyridinyloxyphenoxypropanols of the present invention are similarly prepared by employing procedures analogous to those set forth in the above example and the foregoing teachings of the specification. Such compounds include the following:

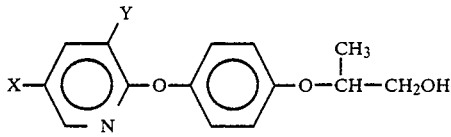

| | | Refractive Index @ | Elemental Analysis, % By Weight* | | | |
|---|---|---|---|---|---|---|
| X | Y | 25° C. | C | H | N | Cl |
| CF$_3$ | Cl | 1.5377 | 51.75 | 3.91 | 4.04 | 10.32 |
| | | | (51.81) | (3.77) | (4.03) | (10.2) |
| CF$_3$ | — | | | | | |
| CF$_3$ | Br | | | | | |
| Cl | CF$_3$ | | | | | |
| Br | CF$_3$ | | | | | |

*Theoretical composition shown in parenthesis

EXAMPLE 9

2-(4-((3,5-bis(triflouromethyl)-2-pyridinyl)-oxy)-phenoxy)propanol (5.45 g; 0.0171 mols) were taken up in 75 ml of toluene and placed in a round bottom reaction flask and 1.8 g of triethylamine was added thereto. Then octoyl chloride (3.05 g; 0.01875 mols) as a solution in 18 ml of toluene was added to the propanol over a 3 minute period at a temperature in the range of 25°–30° C. The mixture was stirred for about an hour at ambient room temperature and then refluxed for about one hour. At the end of the reaction period, the separated hydrochloride salt was filtered off and the toluene was stripped off on a rotary evaporator. The residue was poured into ice water and taken up by extraction with heptane. The heptane extracts were dried and the heptane was removed by distillation, leaving an oil with a refractive index of 1.4740 at 25° C. The anticipated product was 2-(4-((3,5-bis(triflouromethyl)-2-pyridinyl)oxy)phenoxy)propyl octanoate. The product had the following elemental analysis:

| | C | H | N |
|---|---|---|---|
| Calculated | 56.80 | 5.36 | 2.76 |
| Found | 58.0 | 5.88 | 2.79 |

Other propyl esters of the present invention are similarly prepared by employing procedures analogous to those set forth in the above example and the foregoing teachings of the specification. Such other active ingredients include the following compounds:

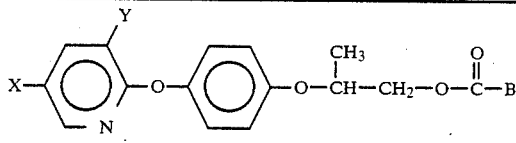

| X | Y | B | Refractive Index @ 25° C. | Elemental Analysis, % By Weight* | | | |
|---|---|---|---|---|---|---|---|
| | | | | C | H | N | Cl |
| $CF_3$ | Cl | $-CH_3$ | 1.5230 | 52.26 (52.38) | 3.99 (3.88) | 3.69 (3.59) | 9.38 (9.10) |
| $CF_3$ | — | $-(CH_2)_6CH_3$ | | | | | |
| $CF_3$ | Cl | $-C_2H_5$ | | | | | |
| $CF_3$ | Br | $-CH_3$ | | | | | |
| $CF_3$ | $CF_3$ | $-i-C_3H_7$ | | | | | |
| Cl | $CF_3$ | $-(CH_2)_2-O-C_2H_5$ | | | | | |

*Theoretical composition shown in parenthesis

EXAMPLE 10

Sodium hydride (0.8 g; 0.0334 mols) is dissolved in 30 ml of dry dimethyl formamide and then a solution of 2-(4-((3,5-bis(trifluoromethyl)-2-pyridinyl)oxy)phenoxy)propanol (5.5 g, 0.0176 mols) in 50 ml of dry dimethylformamide is added to the sodium hydride solution over a four minute period and then stirred for an hour at 40°–50° C. A solution of 1-bromobutane (2.4 g; 0.0175 mols) in 25 ml of dry dimethylformamide is then added over a six minute period. The reaction mixture is then slowly heated to 90° C. over a 30 minute period and held at 90° C. for an hour and ten minutes. The reaction mixture is then stirred and heated at 105°–115° C. for 2 hours. The dimethylformamide is then stripped off under partial vacuum and the crude product poured into cold water and extracted with heptane. The heptane is removed by distillation leaving an oil as product.

Other active ingredients of the present invention are similarly prepared by employing procedures analogous to those set forth in the above example and the foregoing teachings of the specification. Such other active ingredients include the following compounds:

| X | Y | E |
|---|---|---|
| $CF_3$ | $CF_3$ | $-C_2H_5$ |
| $CF_3$ | — | $-CH_3$ |
| Cl | $CF_3$ | $-n-C_4H_9$ |
| $CF_3$ | Br | $-i-C_3H_7$ |
| $CF_3$ | Cl | —⟨phenyl⟩ |
| $CF_3$ | — | —⟨phenyl⟩—Cl |
| $CF_3$ | Cl | $-SO_2Na$ |

EXAMPLE 11

The following series of preparations illustrate an alternate method of synthesizing the propanoate esters and from such compounds the propanoic acids of the invention. A solution of the sodium salt of 4-methoxy phenol was prepared by dissolving the methoxy phenol (7.45 g; 0.06 mole) in 45 ml of dimethylsulfoxide and adding a solution of sodium hydroxide (2.4 g; 0.06 mole) in 7 ml of water. A solution of 2-chloro-5-(trifluoromethyl)pyridine (9.0 g; 0.05 mole) in 40 ml of dimethylsulfoxide was then added to the above sodium phenate solution over an 11 minute period. During the addition, the temperature rose to about 80° C. and then the reaction mixture was heated to 124° C. over a 26 minutes interval and the temperature maintained for 15 minutes. At the end of this time, the reaction mixture was cooled to 75° C. and poured over ice. The solid product was collected on a filter, washed and taken up in a toluene-hexane mixture. This solution on cooling yielded 9.7 grams of solid product having a melting temperature of 49.5°–50.5° C. and having a composition of 58.02% carbon; 3.86% hydrogen; and 5.22% nitrogen. The theoretical composition is 57.99% carbon; 3.74% hydrogen; and 5.20% nitrogen, confirming the product to be 5-(trifluoromethyl)-2-(4-methoxyphenoxy)pyridine.

The 5-(trifluoromethyl)-2-(4-methoxyphenoxy)-pyridine (10.95 g; 0.0407 mole) was refluxed with 5 ml of 48 percent by weight aqueous hydrobromic acid solution for one hour. At the end of this time, the reaction mixture was cooled, poured over ice and the separated solids collected on a filter. The product was purified by taking it up in dilute caustic solution, extracting the solution with chloroform to remove unreacted starting material and then acidifying the solution to precipitate free phenol. The dried crystalline phenol product had a melting temperature of 89°–91° C. and was found to contain 56.21% carbon; 3.27% hydrogen; and 5.44% nitrogen. The theoretical composition of 4-(5-(trifluoromethyl)-2-(pyridinyl)oxy)phenol is 56.48% carbon; 3.16% hydrogen; and 5.49% nitrogen.

The 4-(5-(trifluoromethyl)-2-(pyridinyl)oxy)-phenol (4.95 g; 0.0194 mole) was dissolved in dimethylsulfoxide (41 ml) as reaction medium, then sodium hydroxide (0.78 g; 0.014 mole) was added as a dry powder and the mixture stirred for about 10 minutes and warmed to about 80° C. Ethyl-2-bromopropionate (4.2 g; 0.0233 mole) was then added in one portion and the mixture stirred for about 35 minutes at 96° C. The solution was then cooled, poured over ice and the oil which separated taken up in petroleum ether containing 20 percent by volume methylene chloride. The separated solvent phase was stripped of solvent leaving an oily product weighing 6.3 g. An infrared scan of a sample of the oil confirmed the ester structure of the anticipated ethyl-2-(4-(5-(trifluoromethyl)-2-pyridinyl)-oxy)phenoxy)propionate.

Ethyl-2-(4-(5-(trifluoromethyl)-2-pyridinyl)oxy)-phenoxy)propionate (6.3 g; 0.0177 mole) was dissolved in 28 ml of 2-B-ethanol and a solution of sodium hydroxide (1.06 g; 0.0266 mole) in 28 ml of water was added. The reaction mixture was heated to 75° C. for 5 minutes and then poured into 150 ml of cold water and acidified with 4 g of concentrated hydrochloric acid. The crude acid product which precipitated was washed with hot petroleum ether and dried. The resulting product exhibited a melting temperature of 97°–100° C. and was found on analysis to contain 54.91% carbon; 3.77% hydrogen; and 4.28% nitrogen. The theoretical composition for 2-(4-(5-trifluoromethyl)-2-pyridinyl)oxy)phenoxy)propionic acid is 55.05% carbon; 3.70% hydrogen; and 4.28% nitrogen, indicating the expected product was obtained.

Other active ingredients of the present invention in which Z in the structural formula set forth is

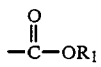

are similarly prepared by employing procedures analogous to those set forth in the above example and the foregoing teachings of the specification by reacting the appropriately substituted 2-halopyridine with 4-methoxy phenol, hydrolyzing the 4-methoxy group to a 4-hydroxy group, and condensing the pyridinyloxy phenol with an alkyl 2-bromopropanoate ester, the ester being then hydrolyzed if it is desired to obtain the propanoic acid form of the compound.

EXAMPLE 12

4-Mercaptophenol (7.6 gm., 0.06 moles) was dissolved in 70 ml of dimethyl(sulfoxide and a solution of sodium hydroxide (2.4 gm., 0.6 moles) in 3.0 ml of water was added. The mixture was warmed to 50° and stirred under nitrogen for 10 minutes to form the sodium thiophenate salt. A solution of 2-chloro-5-(trifluoromethyl)pyridine (10.9 gm., 0.06 moles) in 60 ml of dimethylsulfoxide was then added all at once. The mixture was heated to 100° and held there for 1½ hours. At the end of this time it was poured into 500 ml of cold water. An emulsion formed therefore 60 ml of a saturated solution of ammonium chloride was added. The product precipitated as a sticky solid. The aqueous layer was decanted, the solid washed with more water then taken up in hot heptane, dried with solid sodium sulfate and decolorized with Norite. In the fitrate a white solid product precipitated and was separated and found to have a melting temperature of 89°–93° C.

The so-prepared 4-((5-(trifluoromethyl)-2-pyridinyl)-thio)phenol (10 gms., 0.037 moles) was dissolved in 80 ml of dimethylsulfoxide and dry powdered sodium hydroxide (6.7 gm., 0.37 moles) was added. The mixture was warmed to about 40° and stirred until the base was all in solution indicating that the desired sodium phenate had formed. Ethyl bromopropionate (6.7 gm., 0.37 moles) was then added all at once. The reaction was run at 100°–105° for 2.0 hours, then cooled and poured into 450 ml of cold water. The ester was extracted into methylene chloride, the extract dried and solvent removed leaving the product as an oil weighing 13.5 gm.

This was used without further purification for the next step which was hydrolysis of the ester to the metal salt in aqueous alkaline medium.

The ethyl-2-(4-((5-trifluoromethyl)-2-pyridinyl)-thio)phenoxy)propionate (13.5 gm., 0.37 moles) was dissolved in 50 ml of 95% ethanol and a solution of sodium hydroxide (3.0 gm., 0.075 moles) in 25 ml of water was added. The mixture was refluxed at 80° for about 6.0 minutes then cooled, poured into 400 ml of cold water and extracted with 250 ml of methylene chloride to remove any base insoluble impurities. The aqueous solution containing the sodium salt of the acid was acidified to pH 1 with concentrated hydrochloric acid. The product which precipitated as a gummy solid was washed with water (after decanting) and taken up in hot methylcyclohexane. On cooling the product precipitated as white crystals having a melting temperature of 118°–120° C. and a composition of, by weight, 52.38% carbon; 3.66% hydrogen; 4.00% nitrogen and 9.07% sulfur. The theoretical composition of 2-(4-((5-trifluoromethyl)-2-pyridinyl)thio)phenoxy)-propanoic acid is 52.5% carbon; 3.5% hydrogen; 4.08% nitrogen and 9.34% sulfur.

EXAMPLE 13

4-Mercaptophenol (6.4 gm., 0.051 moles) was dissolved in 70 ml of dimethylsulfoxide and a solution of sodium hydroxide (2.04 gm., 0.051 moles) in a 3.0 ml of water was added. The mixture was warmed to about 50° and stirred under nitrogen for 10 minutes to form the sodium thiophenate salt. A solution of 2,3-dichloro-5-(trifluoromethyl)pyridine (11.0 gm., 0.051 moles) in 60 ml of dimethylsulfoxide was next added all at once. The mixture was then heated at 95°–100° for 2.5 hours. At the end of this time it was poured into 500 ml of cold water and allowed to stand for 45 minutes. The solid was then collected on a filter, washed and taken up in about one liter of boiling hexane. The product precipitated on cooling as a white solid melting at 94°–96° C.

The so-prepared 4-((3-chloro-5-(trifluoromethyl)-2-pyridinyl)thio)phenol (11.0 gm., 0.036 moles) was dissolved in 80 ml of dimethylsulfoxide and dry powdered sodium hydroxide (1.44 gm., 0.036 moles) was added. The mixture was warmed and stirred until the base was all in solution showing that the desired sodium phenate had formed. Ethyl bromopropionate (6.5 gm., 0.036 moles) was then added all at once. The reaction was run at 100° for 2.0 hours then cooled and poured into 500 ml of water. Most of the product precipitated as a white semi-solid. The aqueous layer which was decanted off was extracted with 300 ml of methylene chloride. The extract was separated, solvent removed and the residue added to the main product. This was washed thoroughly with water to remove residual dimethylsulfoxide and used without further purification for the hydrolysis step.

The so-prepared ethyl-2-(4-((3-chloro-5-(trifluoromethyl)-2-pyridinyl)thio)phenoxy)propionate (14.6 gm., 0.036 moles) was dissolved in 60 ml of 95% ethanol and a solution of sodium hydroxide (2.9 gm., 0.072 moles) in 25 ml of water was added. The mixture was heated at reflux for about 4 minutes, then cooled and poured into 400 ml of water. The solution was acidified to pH 1 with concentrated hydrochloric acid which precipitated the product as a sticky solid. This was taken up in a boiling mixture of hexane and methyl cyclohexane. After drying, filtering and cooling, the white crystalline product separated and was collected on a filter and exhibited a melting temperature of 132°-134° C. and was found to contain, by weight, 47.64% carbon; 3.14% hydrogen; 3.51% nitrogen; 9.25% chlorine and 8.44% sulfur. The theoretical composition of 2-(4-((3-chloro-5-trifluoromethyl)-2-pyridinyl)thiophenoxy)propanoic acid is 47.69% carbon; 2.93% hydrogen; 3.70% nitrogen; 9.38% chlorine and 8.48% sulfur.

EXAMPLE 14

Ninety ml of thionyl chloride were added to 9.0 g of 2-(4-((3-chloro-5-(trifluoromethyl)-2-pyridinyl)oxy)-phenoxy)propanoic acid and the mixture was refluxed for 34 minutes. The excess thionyl chloride was removed on a still and the resulting acid chloride was put in solution in 30 ml of benzene. This was added to a reaction flask containing 2.1 g methoxy amine hydrochloride in 20 ml of benzene plus a solution of 3.8 g of potassium carbonate in $3\frac{1}{2}$ ml of water. The reaction mixture was then reflux for 2 hours. The salt was filtered off and the volatiles removed on the rotary evaporator. The crude solids were taken up in heptane and crystallized. From this 6.75 g of white solid were obtained which had a melting point of 135°-6° C. and an elemental analysis of, by weight: C=48.98%, H=3.69%; N=7.16%; and Cl=8.90%. The theoretical composition of 2-(4-((3-chloro-5-(trifluoromethyl)-2-pyridinyl)oxy)phenoxy)-N-methoxy-propanamide is C=49.18%; H=3.61%; N=7.17%; and Cl=9.07%.

EXAMPLE 15

Sixty ml of thionyl chloride were added to 6.0 g of 2-(4-(3-chloro-5-(trifluoromethyl)-2-pyridinyl)oxy)-phenoxy) propanoic acid and the mixture was refluxed for 30 minutes. The excess thionyl chloride was removed on a still using aspirator vacuum. The resulting acid chloride was put in solution in 25 ml toluene. This solution was then added to a reaction flask containing 2.1 g butoxy ethanol (DOWANOL EB®), 1.85 g triethyl amine and and 27 ml toluene and the mixture refluxed for about 2 hours. The salt was filtered off and the volatiles removed on a rotary evaporator. The crude product was taken up in n-hexane, purified with norite activated carbon and the hexane removed on the rotary evaporator. 7.05 g of amber oil were obtained which had a refractive index of 1.5061 at 25° C. and an elemental analysis of: C=54.27%; H=4.97%; N=3.21%; and Cl=7.77%. Calculated values for 2-(4-((3-chloro-5-(trifluoromethyl)-2-pyridinyl)oxy)phenoxy)-propanoic acid, 2-butoxyethyl ester are: C=54.61%; H=5.02%; N=3.03%; and Cl=7.68%.

EXAMPLE 16

Eighty ml of thionyl chloride were added to 8.0 g of 2-(4-(3-chloro-5-(trifluoromethyl)-2-pyridinyl)oxy)-phenoxy)propanoic acid and the mixture was refluxed for 38 minutes. The excess thionyl chloride was then removed on a still using aspirator vacuum. The resulting acid chloride was put into solution in 30 ml toluene. This solution was then added to a reaction flask containing 2.1 g of butyl mercaptan, 2.5 g of triethyl amine and 25 ml of toluene. The mixture was slowly heated to 98° C. over a one hour period and then taken to reflux and refluxed for about 45-50 minutes. The salt was filtered out and the volatiles removed on a rotary evaporator. The crude product was taken up in n-hexane, purified with norite activated carbon and the hexane removed on the rotary evaporator. The resulting 9.1 g of amber oil and a refractive index of 1.5330 at 25° C. and an elemental analysis of: C=52.39%; H=4.46%; N=3.32%; Cl=8.08%; and S=7.1%. The theoretical composition for 2-(4-((3-chloro-5-(trifluoromethyl)-2-pyridinyl)-oxy)phenoxy) propanoic acid-S-butyl ester is: C=52.59%; H=4.41%; N=3.23%; Cl=8.17%; and S=7.39%.

The compounds of the present invention have been found to be suitable for use in methods for the pre and postemergent control of annual and perennial grassy weeds. The active ingredients of the present invention has been found to have advantage over prior art compounds in the control of perennial grassy weeds in that the present compounds control a broader spectrum of such weeds than the counterpart compounds while exhibiting a higher level of activity or control at like dosage rates. In addition, the present compounds are sufficiently tolerant towards most broad leafed crops to contemplate control of grassy weeds therein at substantially commercially practicable levels, particularly so with the preferred compounds.

For all such uses, unmodified active ingredients of the present invention can be employed. However, the present invention embraces the use of a herbicidally-effective amount of the active ingredients in composition form with an inert material known in the art as an adjuvant or carrier in solid or liquid form. Thus, for example, an active ingredient can be dispersed on a finely-divided solid and employed therein as a dust. Also, the active ingredients, as liquid concentrates or solid compositions comprising one or more of the active ingredients can be dispersed in water, typically with aid of a wetting agent, and the resulting aqueous dispersion employed as a spray. In other procedures, the active ingredients can be employed as a constituent of organic liquid compositions, oil-in-water and water-in-oil emulsions or water dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

As organic solvents used as extending agents there can be employed, e.g., benzene, toluene, xylene, kerosene, diesel fuel, fuel oil, and petroleum naptha, ketones such as acetone, methylethyl ketone and cyclohexanone, chlorinated hydrocarbons such as carbon tetrachloride, chloroform, trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butylcarbitol acetate and glycerine. Mixtures of water and organic solvents, either as emulsions or solutions, can be employed.

The active ingredients can also be applied as aerosols., e.g., by dispersing them by means of a compressed gas such as one of the hydrocarbon successors to the fluorocarbons which are shortly to be banned.

The active ingredients of the present invention can also be applied with solid adjuvants or carriers such as talc, pyrophyllite, synthetic fine silica, attapulgus clay, kieselguhr, chalk, diatomaceous earth, lime, calcium carbonate, bentonite, Fuller's earth, cotten seed hulls, wheat flour, soybean flour, pumice, tripoli, wood flour, walnut shell flour, redwood flour and lignin.

As stated, it is frequently desirable to incorporate a surface-active agent in the compositions of the present invention. Such surface-active or wetting agents are advantageously employed in both the solid and liquid compositions. The surface-active agent can be anionic, cationic or nonionic in character.

Typical classes of surface-active agents include alkyl sulfonate salts, alkylaryl sulfonate salts, alkylaryl polyether alcohols, fatty acid esters of polyhydric alcohols and the alkylene oxide addition products of such esters, and addition products of long-chain mercaptans and alkylene oxides. Typical examples of such surface-active agents include the sodium alkylbenzene sulfonates having 10 to 18 carbon atoms in the alkyl group, alkyl phenol ethylene oxide condensation products, e.g., p-isooctylphenol condensed with 10 ethylene oxide units, soaps, e.g., sodium stearate and potassium oleate, sodium salt of propylnaphthalene sulfonic acid, di(2-ethylhexyl)ester of sodium sulfosuccinic acid, sodium lauryl sulfate, sodium decane sulfonate, sodium salt of the sulfonated monoglyceride of coconut fatty acids, sorbitan sesquioleate, lauryl trimethyl ammonium chloride, octadecyl trimethyl ammonium chloride, polyethylene glycol glauryl ether, polyethylene glycol esters of fatty acids and rosin acids, e.g., Ethofat 7 and 13, sodium N-methyl-N-oleyl taurate, Turkey Red Oil, sodium dibutylnaphthalene sulfonate, sodium lignin sulfonate, polyethylene glycol stearate, sodium dodecyl benzene sulfonate, tertiary dodecyl polyethylene glycol thioether (nonionic 218), long-chain ethylene oxide-propylene oxide condensation products, e.g., Pluronic 61 (molecular weight about 1000), polyethylene glycol ester of toll oil acids, sodium octophenoxyethoxyethyl sulfate, tris(polyoxyethylene)sorbitan monostearate (Tween 60), and sodium dihexylsulfosuccinate.

The concentration of the active ingredients in solid or liquid compositions generally is from about 0.003 to about 95 percent by weight or more. Concentrations from about 0.05 to about 50 percent by weight are often employed. In compositions to be employed as concentrates, the active ingredient can be present in a concentration from about 5 to about 98 weight percent. The active ingredient compositions can also contain other compatible additaments, for example, phytotoxicants, plant growth regulants, pesticides and the like and can be formulated with solid particulate fertilizer carriers such as ammonium nitrate, urea and the like.

The present compositions can be applied by the use of power dusters, boom and hand sprayers, spray dusters, by addition to irrigation water, and by other conventional means. The compositions can also be applied from airplanes as a dust or a spray since the active ingredients are effective at very low application rates.

The active ingredients of the present invention including methyl 2-((4-(5-trifluoromethyl)-2-pyridinyl)-oxy)phenoxy)propanoate; 2-((4-(5-trifluoromethyl)-3-chloro-2-pyridinyl)oxy)phenoxy)propionamide; 2-((4-(5-(trifluoromethyl)-2-pyridinyl)oxy)phenoxy-propanoic acid and salts thereof according to the present invention; butyl 2-((4-(5-trifluoromethyl)-3-chloro-2-pyridinyl)oxy)phenoxypropanoate; 2-((4-(5-trifluoromethyl)-2-pyridinyl)-oxy)phenoxy)propionamide N-methyl 2-((4-(5-trifluoromethyl)-2-phridinyl)oxy)-phenoxy)propanomide and 2-(4-((3-chloro-5-trifluoromethyl-2-pyridinyl)thio)phenoxy propanoic acid have been found to possess desirable herbicidal activity in general against grassy weeds such as foxtail, barnyard grass, wild oats and crabgrass in preemergent operations and also against the same grasses and particularly seedling Johnson grass in postemergent operations. These compounds possess unique activity in being effective in the control broadly of all or most of Johnson grass, quack grass, bermuda grass, orchard grass, Dallis grass and cogon grass, all perennial grassy weeds, while being tolerant to fairly tolerant to broadleaf crops such as cotton and soybeans.

The active ingredients of the present invention including the compounds just above listed have been found to possess particularly desirable herbicidal activity against wild oats, foxtail, barnyard grass, crabgrass and seedling Johnson grass in postemergent operations, as well as desirable broad spectrum activity against the perennial grassy weeds listed above and at lower dosage rates than the substituted propanoates and propanols of the prior art while showing a greater tolerance to broad leaf crops.

The present compounds which are substituted propanols or propyl ethers are more effective in preemergent operations than in postemergent applications.

The exact rate to be applied is dependent not only on a specific active ingredient being applied, but also on a particular action desired (e.g., general or selective control), the plant species to be modified and the stage of growth thereof as well as the part of the plant to be contacted with the toxic active ingredient. Thus, it is to be understood that all of the active ingredients of the present invention and compositions containing the same may not be equally effective at similar concentrations or against the same plant species. In non-selective pre-emergence and foliar treatments, the active ingredients of the invention are usually applied at an approximate rate of from about 0.5 to about 5 pounds/acre, but lower or higher rates may be appropriate in some cases such as 0.01 to about 20 pounds/acre or more. In preemergent operations for selective uses a dosage of about 0.05 to about 20 pounds/acre or more is generally applicable, a rate of 0.2 to 4 pounds/acre being preferred and about 0.75 to about 1 pound/acre being most preferred.

In selective postemergent operations a dosage of about 0.01 to about 20 pounds/acre or more is generally applicable, although not all compounds are equally effective and some weeds are more difficult to control. Thus, a dosage rate in the range of about 0.05 to about 0.75 pounds/acre is preferred in postemergent control of annual grassy weeds, while about 0.5 to about 5 pounds/acre is a preferred dosage range for the postemergent control of perennial grassy weeds.

In view of the foregoing and following disclosures, one skilled in the art can readily determine the optimum rate to be applied in any particular case.

EXAMPLES 17–40

In representative operations, each compound to be utilized in a series of tests is dissolved in acetone to one half of the final volume (twice the final concentration) to be used and the acetone solution in each case is admixed with an equal volume of water containing 0.1 percent by weight of Tween-20 surface active material (Tween 20 is a trademark of Atlas Chemical Company). Each compound is selected from a group consisting of compounds according to the invention. The compositions, generally in the nature of an emulsion, were employed to treat separate respective seed beds of sandy loam soil of good nutrient content wherein each seed bed contained separate groups of a known number of good viable seeds, each group being of one of a predetermined plant species. The various beds were positions side by side and exposed to substantially identical conditions of temperature and light. Each bed was maintained so as to prevent any interaction with test compounds in different seed beds. Each seed bed was treated with one of the compositions as a soil drench applied at one of two predetermined rates to deposit a predetermined amount of a given test compound uniformly throughout the surface of the bed. The compositions were applied to the seed beds so that different seed beds of a given plant species were treated with one of each of the test compounds. Another seed bed was treated only with water to serve as a control. After treatment, the seed beds were maintained for two weeks under greenhouse conditions conducive for good plant growth and watered as necessary. The specific plant species, test compound and dosage and the percent preemergent control obtained are set forth in the table below. Control refers to the reduction in growth compared to the observed results of the same species.

PREEMERGENCE CONTROL OF PLANT SPECIES

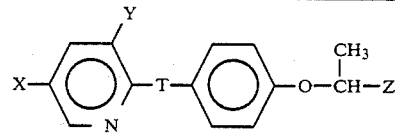

| | Compound Tested | | | Dosage In | Plant Species | | | | | | | |
|---|---|---|---|---|---|---|---|---|---|---|---|---|
| X | Y | Z | T | Lbs Per Acre | Corn | Rice | Wheat | Wild Oats | Foxtail | Barnyard Grass | Crabgrass | Johnson Grass |
| Cl | CF$_3$ | —CN | O | 1 | 95 | 70 | 0 | 40 | 100 | 95 | 100 | 100 |
| | | | | .25 | 40 | 0 | 0 | 0 | 95 | 0 | 40 | 70 |
| CF$_3$ | — | —C(O)—OCH$_3$ | O | 0.5 | 100 | 100 | 100 | 100 | 100 | 100 | 100 | 100 |
| | | | | 0.125 | 100 | 80 | 100 | 100 | 95 | 98 | 100 | 100 |
| | | | | 0.063 | 60 | 0 | 20 | 100 | 90 | 60 | 90 | 98 |
| Cl | CF$_3$ | —C(O)NH$_2$ | O | 1 | 100 | 90 | 100 | 100 | 100 | 100 | 100 | 100 |
| | | | | 0.25 | 60 | 20 | 70 | 80 | 80 | 60 | 100 | 80 |
| CF$_3$ | Cl | —C(O)NHCH$_3$ | O | 0.5 | 100 | 98 | 100 | 70 | 100 | 100 | 100 | 100 |
| | | | | .125 | 80 | 0 | 90 | 0 | 90 | 99 | 100 | 80 |
| CF$_3$ | — | —C(O)—NH$_2$ | O | 0.5 | 100 | 100 | 100 | 100 | 100 | 100 | 100 | 100 |
| | | | | .125 | 95 | 60 | 90 | 60 | 98 | 100 | 100 | 95 |
| CF$_3$ | CF$_3$ | —CN | O | 10 | — | — | — | 40 | 95 | 100 | 100 | — |
| CF$_3$ | — | —C(O)—O—CH$_3$ | O | 10 | — | — | — | 100 | 100 | 100 | 100 | — |
| CF$_3$ | Cl | —C(O)—OH | S | 0.125 | 100 | 100 | 30 | 95 | 95 | 100 | 100 | 97 |
| | | | | .063 | 98 | 100 | 20 | 50 | 90 | 100 | 100 | 97 |
| Cl | CF$_3$ | —C(O)—O—C$_4$H$_9$ | O | 1 | 100 | 98 | 40 | 90 | 100 | 100 | 100 | 90 |
| | | | | .25 | 61 | 0 | — | 40 | 60 | 100 | 90 | 90 |
| CF$_3$ | CF$_3$ | —CH$_2$O—C(O)(CH$_2$)$_6$CH$_3$ | O | 1 | 70 | 0 | 60 | 90 | 80 | 60 | 100 | 90 |
| | | | | .25 | 0 | — | 20 | 70 | 80 | 0 | 90 | 60 |
| CF$_3$ | — | —CN(CH$_3$)$_2$ | O | 1 | 70 | 95 | 98 | 90 | 100 | 60 | 100 | 90 |
| | | | | .25 | 0 | 20 | 40 | 0 | 80 | 0 | 98 | 60 |
| CF$_3$ | — | —CN | O | 10 | — | — | — | 100 | 100 | 100 | 100 | — |
| CF$_3$ | Cl | —CN | O | 10 | — | — | — | 100 | 100 | 100 | 100 | — |
| CF$_3$ | CF$_3$ | —COCH$_3$ | O | 10 | — | — | — | 100 | 100 | 100 | 100 | — |
| CF$_3$ | CF$_3$ | —CH$_2$OH | O | 10 | — | — | — | 90 | 98 | 98 | 95 | — |
| CF$_3$ | Cl | —CH$_2$OH | O | 10 | — | — | — | 100 | 100 | 100 | 100 | — |
| CF$_3$ | Cl | —CH$_2$OCCH$_3$ | O | 10 | — | — | — | 100 | 100 | 100 | 100 | — |
| CF$_3$ | Cl | —COC$_4$H$_9$ | O | 10 | — | — | — | 100 | 100 | 100 | 100 | — |

PREEMERGENCE CONTROL OF PLANT SPECIES

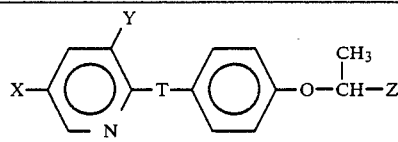

| Compound Tested | | | T | Dosage In Lbs Per Acre | Corn | Rice | Wheat | Wild Oats | Fox-tail | Barn-yard Grass | Crab-grass | Johnson Grass |
|---|---|---|---|---|---|---|---|---|---|---|---|---|
| X | Y | Z | | | | | | | | | | |
| CF₃ | CF₃ | —CO(CH₂)₇CH₃ (O=) | O | 10 | — | — | — | 100 | 100 | 100 | 100 | — |
| CF₃ | Cl | —CNH₂ (O=) | O | 10 | — | — | — | 100 | 100 | 100 | 100 | — |
| CF₃ | Cl | —COCH₃ (O=) | O | 10 | — | — | — | 100 | 100 | 100 | 100 | — |
| Cl | CF₃ | —C—OH (O=) | O | 10 | — | — | — | 100 | 100 | 100 | 100 | — |
| CF₃ | CF₃ | —C—OH (O=) | O | 10 | — | — | — | 100 | 100 | 100 | 100 | — |
| CF₃ | Cl | —C—OH (O=) | O | 10 | — | — | — | 100 | 100 | 100 | 100 | — |
| CF₃ | — | —C—OH (O=) | O | 10 | — | — | — | 100 | 100 | 100 | 100 | — |

EXAMPLES 42–65

So as to illustrate clearly the phytotoxic properties of the various active ingredients of the present invention applied postemergently, a group of controlled greenhouse experiments is described below.

Various species of plants were planted in beds of good agricultural soil in a greenhouse. After the plants had emerged and grown to a height of about 2–6 inches a portion of the plants were sprayed with an aqueous mixture, made by mixing a selected active ingredient and emulsifier or dispersant with about 1:1 water-acetone, employing sufficient amounts of the treating composition to provide application rates of 4000 parts per million (ppm) or about 10 pounds per acre and in some cases at lower rates. Other portions of the plants were left untreated to serve as controls.

After a period of 2 weeks, the effect of the respective test ingredients used on respective groups of plants was evaluated by a comparison with the control groups of the plants. The results are tabulated in the following table.

POSTEMERGENCE CONTROL OF PLANT SPECIES

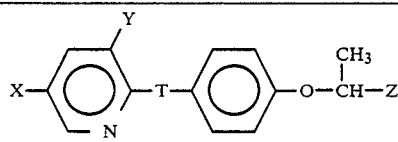

| Compound Tested | | | T | Dosage in PPM | Corn | Rice | Wheat | Wild Oats | Fox-tail | Barn-yard Grass | Crab-grass | Johnson Grass |
|---|---|---|---|---|---|---|---|---|---|---|---|---|
| X | Y | Z | | | | | | | | | | |
| Cl | CF₃ | —COC₄H₉ (O=) | O | 500 | 100 | 0 | 40 | 100 | 100 | 100 | 100 | 100 |
|  |  |  |  | 125 | 80 | — | 0 | 80 | 98 | 100 | 98 | 98 |
| CF₃ | Cl | —CNHCH₃ (O=) | O | 125 | 95 | 98 | 40 | 70 | 100 | 80 | 100 | 100 |
|  |  |  |  | 31.5 | 70 | 90 | 20 | 70 | 98 | 40 | 100 | 100 |
| CF₃ | Cl | —CNH₂ (O=) | O | 62.5 | 100 | 80 | 60 | 80 | 100 | 100 | 100 | 100 |
|  |  |  |  | 15.6 | 100 | 80 | 60 | 98 | 98 | 100 | 99 | 100 |

-continued

POSTEMERGENCE CONTROL OF PLANT SPECIES

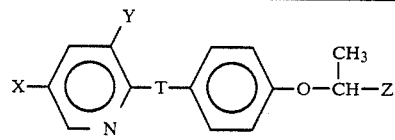

| Compound Tested | | | | | Plant Species | | | | | | | |
|---|---|---|---|---|---|---|---|---|---|---|---|---|
| X | Y | Z | T | Dosage in PPM | Corn | Rice | Wheat | Wild Oats | Fox-tail | Barn-yard Grass | Crab-grass | Johnson Grass |
| CF₃ | Cl | —COH (C=O) | O | 62.5 | 100 | 90 | 95 | 100 | 100 | 100 | 100 | 100 |
| | | | | 15.6 | 100 | 30 | 60 | — | 95 | 100 | 98 | 100 |
| CF₃ | — | —CNH₂ (C=O) | O | 62.5 | 95 | — | 60 | 100 | 100 | 90 | 100 | 100 |
| | | | | 15.6 | 95 | — | 40 | 20 | 60 | 90 | 90 | 98 |
| CF₃ | — | —C—OH (C=O) | O | 62.5 | 100 | 70 | 50 | 80 | 90 | 70 | 98 | 100 |
| | | | | 15.6 | 80 | 40 | 30 | 10 | 90 | 20 | 90 | 95 |
| Cl | CF₃ | —CNH₂ (C=O) | O | 500 | 60 | 0 | 0 | 0 | 0 | 0 | 60 | 100 |
| CF₃ | Cl | —CNHCH₃ (C=O) | O | 62.5 | 80 | 99 | 90 | 98 | 90 | 90 | 98 | 100 |
| | | | | 15.6 | 60 | 60 | 80 | 90 | 80 | 60 | 98 | 100 |
| CF₃ | CF₃ | —CN | O | 4000 | — | — | — | 100 | 90 | 100 | 100 | — |
| Cl | CF₃ | —CN | O | 4000 | — | — | — | — | 80 | 60 | 100 | — |
| Cl | CF₃ | —CNH₂ (C=O) | O | 4000 | — | — | — | 100 | 100 | 100 | 100 | — |
| CF₃ | — | —COCH₃ (C=O) | O | 4000 | — | — | — | — | 100 | 100 | 100 | — |
| CF₃ | — | —CN | O | 4000 | — | — | — | 100 | 100 | 100 | 100 | — |
| CF₃ | Cl | —CN | O | 4000 | — | — | — | 100 | 100 | 100 | 100 | — |
| CF₃ | CF₃ | —COCH₃ (C=O) | O | 4000 | — | — | — | 100 | 100 | 100 | 100 | — |
| CF₃ | CF₃ | —CH₂OH | O | 4000 | — | — | — | 95 | 95 | 70 | 98 | — |
| CF₃ | Cl | —CH₂OH | O | 4000 | — | — | — | 100 | 100 | 100 | 100 | — |
| CF₃ | Cl | —CH₂OCCH₃ (C=O) | O | 4000 | — | — | — | 100 | 100 | 100 | 100 | — |
| CF₃ | Cl | —CO(CH₂)₃CH₃ (C=O) | O | 4000 | — | — | — | 100 | 100 | 100 | 100 | — |
| CF₃ | CF₃ | —C—O—C₈H₁₇ (C=O) | O | 4000 | — | — | — | 99 | 100 | 100 | 100 | — |
| CF₃ | Cl | —C—OCH₃ (C=O) | O | 4000 | — | — | — | 100 | 98 | 100 | 100 | — |
| Cl | CF₃ | —COH (C=O) | O | 4000 | — | — | — | 100 | 100 | 100 | 100 | — |
| CF₃ | CF₃ | —COH (C=O) | O | 4000 | — | — | — | 100 | 100 | 100 | 100 | — |

-continued

POSTEMERGENCE CONTROL OF PLANT SPECIES

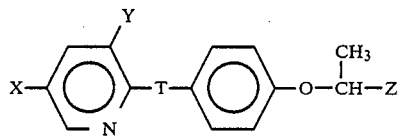

| Compound Tested | | | | | Plant Species | | | | | | |
|---|---|---|---|---|---|---|---|---|---|---|---|
| X | Y | Z | T | Dosage in PPM | Corn | Rice | Wheat | Wild Oats | Fox-tail | Barn-yard Grass | Crab-grass | Johnson Grass |
| CF$_3$ | Cl | O‖—C—OH | S | 28 | 100 | 20 | *— | 60 | 100 | 100 | 100 | 100 |
| | | | | 14 | 30 | 0 | — | 0 | 100 | 80 | 98 | 100 |
| | | | | 7 | 0 | — | — | — | 80 | 30 | 90 | 100 |

*Wheat was not run at these lower dosage rates as control at 111 ppm was only 20% at 55.5 ppm control was zero.
Approximate pounds per acre application equivalent to ppm dosage rates are as flooows: 111 ppm = 0.2 lbs/A; 55.5 ppm = 0.1 lb; 28 ppm = 0.05 lb; 14 ppm = 0.025 lb; 7 ppm = 0.013 lb/A.

EXAMPLES 66–77

In a series of tests clearly demonstrating the herbicidal properties of the compounds of the present invention applied postemergently, various metal and amine salts of propanoic acids prepared in aqueous solution as described hereinabove and brought initially to a dilution of 4,000 ppm were applied to growing plants under greenhouse conditions.

Various species of plants were planted in a series of pots containing good agricultural soil in a greenhouse. After some of the plants had emerged and grown to a height of about 2–6 inches some of the plants were sprayed, respectively, with a respective one of the said aqueous solutions, then diluted and sprayed on other respective selected plants at lower rates, each species of plant not being run at all rates. Other plants were left untreated to serve as controls. Still other plants, plants of Bermuda grass, blue grass, Johnson grass and cheat grass, were allowed to grow to 6–8 inches then four times cut back to 2 inches and allowed to regrow, all over about a 6–7 week period providing established plants.

After a period of about two weeks, the effect of the respective test ingredients used on various respective plants was evaluated by comparison with the control group of plants. The results showed that the potassium and triethylamine salts of 2-((4-(5-(trifluoromethyl)-3-chloro-2-pyridinyl)-oxy)phenoxy)propanoic acid applied (a) at a rate of 4,000 ppm gave complete control of Bermuda grass, sorghum and barnyard grass while showing little or no control of cotton; (b) at a rate of 2,000 ppm gave substantial to complete control of bluegrass and rice while showing no effect on soybeans; (c) at a rate of 1,000 ppm gave complete control of Johnson grass, crabgrass and yellow foxtail; and (d) at a rate of 500 ppm exhibited complete control of cheat grass, corn, wheat and wild oats.

In addition, the ethanolamine and sodium salts of 2-4((-(5-(trifluoromethyl)-2-pyridinyl)oxy)phenoxy)-propanoic acid applied (a) at a rate of 4,000 ppm gave complete control of Bermuda grass, sorghum and barnyard grass while showing no adverse effects on cotton; (b) at a rate of 2,000 ppm gave 70% control of bluegrass and complete control of rice while having no adverse effects on soybeans; (c) at a rate of 1,000 ppm showed complete control of Johnson grass and crab grass and fair to excellent control of yellow foxtail; and (d) at a rate of 500 ppm gave complete control of cheat grass, corn, wheat and wild oats.

Further the ethylamine salt of 2-((4-(5-chloro-3-trifluoromethyl)-2-pyridinyl)oxy)phenoxy)propanoic acid and the ammonium salt of 2-((4-(3,5-bis(trifluoromethyl)-2-pyridinyl)oxy)phenoxy)propanoic acid gave nearly as good control of the same plants at the rates recited above as described for the salts rated in the preceding paragraphs.

The same salts applied in preemergent operations using the solutions described above as well as in Examples 6 and 7 and applied at rates in the range of about 10 to about 1.25 pounds per acre in a manner similar to that described for Examples 17–41 showed substantially complete to complete control of crabgrass, yellow foxtail, barnyard grass, wild oats and wheat and no control of cotton velvet leaf or annual morning glory at the higher rates and the same or substantially the same excellent control at the lower rates.

EXAMPLES 78–79

In preemergent operations carried out in a manner similar to that described in Examples 17–41, using 10 pounds-acre of active ingredient, N,N-di-n-butyl 2-((4-(3,5-bis(trifluoromethyl)-2-pyridinyl)oxy)phenoxy propanamide gave 60 percent control of crabgrass, but no control of wild oats, foxtail, barnyard grass, cotton, pigweed, annual morning glory or velvet leaf, while N,N-dimethyl 2-((4-(5-trifluoromethyl-2-pyridinyl)oxy)phenoxy)propanamide showed complete control of wild oats, foxtail, barnyard grass and crabgrass.

In postemergent operations carried out in the same manner as that described in Examples 42–65, applying active ingredient at the rate of 4,000 ppm, the above described N,N-di-n-butyl propanamide showed 80 percent control of cotton and 60 percent control of velvet leaf but no control of wild oats, foxtail, barnyard grass, crabgrass or annual morning glory, while the above identified N,N-dimethyl propanamide exhibited complete control of wild oats, foxtail, barnyard grass and crabgrass.

What is claimed is:

1. A process for making a pyridyloxyphenol compound having the formula

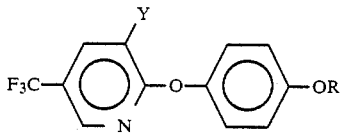

where R is H, a metal cation of a caustic solution or lower alkyl and Y is H, Cl, Br or $CF_3$ which comprises reacting a compound having the formula

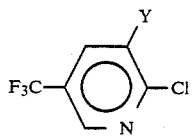

where Y is as above defined, with a compound having the formula

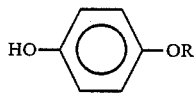

where R is as above defined, in the presence of a caustic solution.

2. Process of claim 1 wherein R is methyl.

3. Process of claim 2 where the resulting product is acidified, forming the free phenol.

4. Process of claim 3 where the free phenol is further reacted with sodium hydroxide forming the sodium phenate.

5. A process for making a compound having the formula

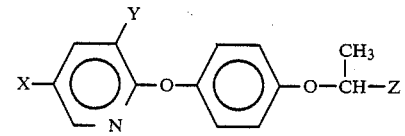

wherein
X is Cl, Br or $CF_3$;
Y is H, Cl, Br or $CF_3$, provided at least one of X and Y is $CF_3$;
Z is

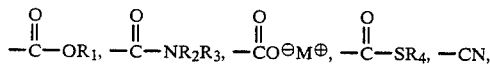

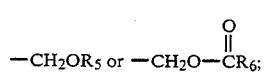

$R_1$ is H, $C_1$–$C_8$ alkyl, benzyl, chlorobenzyl or $C_3$–$C_6$ alkoxyalkyl;
$R_4$ is $C_1$–$C_4$ alkyl;
$R_5$ is H or $C_1$–$C_4$ alkyl;
$R_6$ is $C_1$–$C_7$ alkyl;
M is —$NHR_2R_3R_7$, Na, K, Mg or Ca;
$R_2$ and $R_3$ are each independently $R_7$ or —$OCH_3$, provided both $R_2$ and $R_3$ cannot simultaneously be $OCH_3$ and neither is —$OCH_3$ in —$NHR_2R_3R_7$; and $R_7$ is H, $C_1$–$C_4$ alkyl or $C_2$–$C_3$ hydroxyalkyl, which comprises reacting a compound having the formula

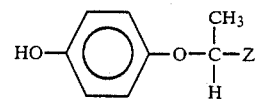

wherein Z is as above defined, with a compound having the formula

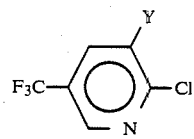

where Y is as above defined, in an inert solvent in the presence of aqueous sodium hydroxide while agitating and heating.

6. Process of claim 5 wherein 2-(4-hydroxyphenoxy)-propanoic acid is reacted with 2,3-dichloro-5-(trifluoromethyl)pyridine.

7. Process of claim 5 wherein 2-(4-hydroxyphenoxy)-propanoic acid is reacted with 2-chloro-5-(trifluoromethyl)pyridine.

8. A process for making a compound having the formula

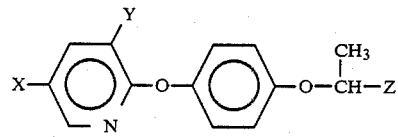

wherein
X is Cl, Br or $CF_3$;
Y is H, Cl, Br or $CF_3$, provided at least one of X and Y is $CF_3$;
Z is

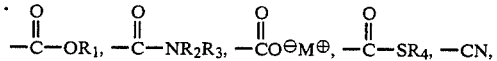

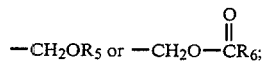

$R_1$ is H, $C_1$–$C_8$ alkyl, benzyl, chlorobenzyl or $C_3$–$C_6$ alkoxyalkyl;
$R_4$ is $C_1$–$C_4$ alkyl;
$R_5$ is H or $C_1$–$C_4$ alkyl;
$R_6$ is $C_1$–$C_7$ alkyl;
M is —$NHR_2R_3R_7$, Na, K, Mg or Ca;
$R_2$ and $R_3$ are each independently $R_7$ or —$OCH_3$, provided both $R_2$ and $R_3$ cannot simultaneously be —$OCH_3$ and neither is —$OCH_3$ in —$NHR_2R_3R_7$; and
$R_7$ is H, $C_1$–$C_4$ alkyl or $C_2$–$C_3$ hydroxyalkyl, which comprises reacting a compound having the formula

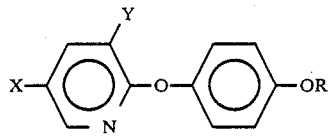

wherein R is H or a metal cation of a caustic solution, with a 2-halopropanoic acid compound in the presence of a base.

9. Process of claim 8 wherein R is sodium and the 2-halopropanoic acid compound is an ester of 2-bromopropanoic acid.

* * * * *

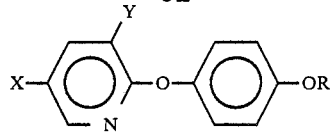

wherein R is H or a metal cation of a caustic solution, with a 2-halopropanoic acid compound in the presence of a base.

9. Process of claim 8 wherein R is sodium and the 2-halopropanoic acid compound is an ester of 2-bromopropanoic acid.

* * * * *